US006244093B1

(12) United States Patent
Parekh

(10) Patent No.: US 6,244,093 B1
(45) Date of Patent: Jun. 12, 2001

(54) METHOD AND APPARATUS FOR CALIBRATING AN AIR MONITOR USING A FLOW MATCHING VALVE

(76) Inventor: Kaushik K. Parekh, 6717-B Polk St., Houston, TX (US) 77011

( * ) Notice: Subject to any disclaimer, the term of this patent is extended or adjusted under 35 U.S.C. 154(b) by 0 days.

(21) Appl. No.: 09/042,329

(22) Filed: Mar. 13, 1998

Related U.S. Application Data

(60) Provisional application No. 60/036,554, filed on Mar. 14, 1997.

(51) Int. Cl.[7] .................................................. G01N 37/00
(52) U.S. Cl. ............................................................ 73/1.06
(58) Field of Search .................................. 73/1.06, 1.07, 73/31.02, 31.01, 31.03, 23.2

(56) References Cited

U.S. PATENT DOCUMENTS

| | | | | |
|---|---|---|---|---|
| 3,467,137 | * | 9/1969 | Brown | 137/494 |
| 3,976,450 | * | 8/1976 | Marcote et al. | 73/31.02 |
| 4,722,217 | * | 2/1988 | Arnett et al. | 73/1.06 |
| 5,402,665 | * | 4/1995 | Hart et al. | 73/1.06 |
| 5,665,894 | * | 9/1997 | Baker | 73/1.06 |

FOREIGN PATENT DOCUMENTS 55-74438 * 6/1980 (JP) ........................................ 73/1.06

* cited by examiner

Primary Examiner—Hezron Williams
Assistant Examiner—Nashmiya Fayyaz
(74) Attorney, Agent, or Firm—Umesh M. Desai

(57) ABSTRACT

The present invention is directed to a new and improved apparatus and methods for calibrating environmental air monitor. A new calibration kit comprising a gas cylinder containing calibration gas, a preset regulator valve, a flow matching valve and tubing is disclosed which overcomes many of the prior art disadvantages. The flow matching valve compensates for deviation in calibration gas flow conditions and thus eliminating the need of a sampling bag. The flow matching valve modifies the preset regulator valve by compensating loss of pressure or flow going to the sensor in the environmental air or gas monitor. In addition when an abundance of pressure or flow is transmitted to the monitor, the flow matching valve "vents-off" the excess calibration gas. A method for calibrating a gas or air monitor is also disclosed. The method and apparatus permits a laminar flow, over a sensor located in the air monitor, of constant quantity and quality that is critically necessary for calibrating air monitors.

5 Claims, 5 Drawing Sheets

METHOD AND APPARATUS FOR CALIBRATING AN AIR MONITOR USING A FLOW MATCHING VALVE

This application claims benefit from provisional application No. 60/036,554 filed Mar. 14, 1997.

BACKGROUND OF THE INVENTION

This invention relates to methods and apparatus for regulating flow of gas from one point to another. For example, the methods and apparatus of this invention may be used to regulate flow of gas from a gas container or cylinder to its intended destination in an environmental monitoring equipment. More particularly, but not by way of limitation, this invention relates to a method and apparatus for regulating the quantity and quality of gas flow from a portable gas container to a device that monitors environmental conditions for the purpose of calibrating the environmental monitor prior to use.

Today's complex industrialized world presents high levels of danger and difficulty for workers of all kinds. Among the more dangerous conditions workers face everyday is the risk of encountering hazardous air. Hazards in the air may range from causing discomfort to causing immediate death. In this range is included explosive gases to subtle health hazards which lead to great harm with repeated exposure over a period of time. The three most common hazards are air containing high levels of a) oxygen, b) toxic gases such as carbon monoxide and hydrogen sulfide, and c) combustible gases including vapors commonly existing as liquids.

Oxygen is an odorless, colorless and tasteless gas that supports life but also makes combustion possible. When oxygen deficiency in air is encountered it becomes a hazard in that such deficiency may result in asphyxiation in confined spaces. On the other hand, too much oxygen may result in an explosive atmosphere. Next, toxic gases may result in death after short exposure or in other cases result in harmful physiological changes caused by repeated long-term exposures. Combustible gases ignite resulting in explosions especially where oxygen is present.

Thus dangerous environments containing unsafe quantities of hazardous air must be detected and avoided or ventilated (made safe). Detection of hazardous air is done through gas detectors or monitors of various types. The specification of the present invention will interchangeably use gas detectors or monitors with the intent that they mean the same item. Gas detectors or monitors are commonly used in the following situations: a) any entry into a confined space; b) any "hot-work" spaces such as welding, cutting or using electrical items in and around potentially combustible gases; c) time-weighted average personal exposure monitoring such as exposure to a given toxic gas over some period of time; d) leak detection as in where a known gas is leaking; and e) an emergency response—especially when conditions are unknown. Thus, armed with correct information, any worker may be assisted in approaching an environment with safety.

Many conventional gas detectors employ various sensing technologies to be able to detect the presence of one or more potential gas hazards. The central element to all of the various sensing technologies is that sensor in the gas detector has a known steady state parameter in normal clean air and that parameter changes as it comes into contact with the gas or gases intended to be monitored. It is this change in the parameter from the known starting point that allows the measurement of the various gases in the air.

Current sensor technologies include a) electro-chemical sensors, commonly used for detection of oxygen and toxic gases, b) catalytic beads or pellistors, commonly used for detection of combustible gases, and c) metal oxide sensors, a newer form of sensor used for detection of combustible and toxic gases. Combination of the these three sensing technologies are most commonly found in portable personal safety gas detectors. Other more sophisticated devices include photo-ionization detection and flame ionization detection.

Electro-chemical sensors have a housing containing a specially mixed electrolyte which is intended to react with a gas (or gases) that is (are) intended to be monitored while not reacting with other gases that may also be present in the air. Depending on the type of electrolyte, the sensor may be more or less sensitive unless the monitor is calibrated. The catalytic beads or pellistors actually oxidize or burn the gas as it passes over the electric wire filaments in the sensor. One of the circuits in the sensor is specially treated with various catalysts to allow it to react differently with the burning gas than other untreated wire filaments in the sensor. By measuring the change in the electrical properties between the treated portion of the circuit and the untreated portion of the circuit, the sensor is able to give an indication of gas presence and level. Metal oxide sensors also operate on the principle of changing electrical properties within the circuits due to the exposure to various gases.

As a result of the very sensitive nature of these various sensors, it is extremely important that the gas monitors or detectors be calibrated often to obtain accurate sensor readings. As in the case of periodic tuning of a car, a gas monitor or detector needs tuning on a frequent basis. The checking for accuracy of sensors is accomplished by exposing the sensors to a known level of gas and taking readings; for example, a gas detector containing a combustible sensor, an oxygen sensor and a carbon monoxide sensor is exposed to a premixed gas of various levels of oxygen, carbon monoxide and a known combustible. If after exposure, the readings obtained from the gas detector agree with the predetermined and known levels of the premixed gas, the detector is in calibrated and may be safely used. However, if one or more of the readings varies from the known levels in the premixed gas, the detector must be calibrated according to the calibration instructions and once the reading agrees with the premixed gas, the detector may be safely used. If the sensors do not respond or fail to remain calibrated, such condition provides an indication that there is a fault in the unit or very possibly that the sensor itself has degraded to the point where it must be replaced.

The apparatus used to calibrate gas detectors comprises a calibration kit. It must be understood that to obtain the most accurate calibration of the gas monitor, it is very important that the flow of the sampling gas must be smooth, consistent and most nearly simulate the environmental conditions. The process of calibration is performed in a well ventilated location by slowly proceeding to open the gas container or cylinder by adjusting its regulator valve and allowing flow of the required gas to flow to the gas monitor or detector. After about three or so minutes of gas flow, gas readings are taken and verified that the respective sensor's reading matches with the known gas concentration parameter. Again, it cannot be over-emphasized that the condition of the gas flow determines to a great degree the quality of the calibration of the monitor.

One problem, most often, encountered in this type of calibration process is that the flow of gas to the detector is not well regulated and therefore the readings become unreliable. For example, if the gas flow varies in flow quantity, the sensor reading will accordingly vary simply because the exposure is different at every moment in time as the reading is observed.

As a result, a common industry custom developed to overcome this flow control problem by installing a sampling bag between the regulator valve and the gas monitor. The convention has been to fill up the bag with the calibration gas of known concentration by opening the valve for some time and then adjusting it to closed or nearly closed position as the bag is filled up. The bag is then squeezed and the calibration gas is then pumped into the gas monitor with the help of a aspirator pump located in the gas monitor as needed. Obviously, there is great potential for error and studies have shown that the gas monitor encounters differing readings as the bag deflates.

In addition to the above problem, severe other problems are encountered in using this prior art technology in that the calibration gas is diluted at times and contaminated at other times. Still further, the calibration gas is absorbed and diffused in the bag at other times.

Another disadvantage or severe problem encountered by the conventional method of calibration is that the draw rate of the pump in the gas detector or monitor varies from pump to pump. This variance in pump draw rate cannot be compensated by the current technology since the flow regulator valves operate at preset values. Another related problem is that the gas container or cylinder pressure varies as the quantity of gas decreases. Thus with simple preset flow regulators, as the pressure goes down, the flow condition out of the regulator valve changes resulting in relative flow variances and resulting fluctuating (and unreliable) sensors readings. Similarly, as the battery power supply wears down, pump draw rates also begin to vary and again resulting in unreliable readings. Thus conventional apparatus and method of calibrating gas detectors is cumbersome and possesses many disadvantages as well as dangers. Therefore, there is a desperate need for a new apparatus or device and method which permits gas flow which matches fluctuation and changes in flow while operating in a safe manner.

SUMMARY OF THE INVENTION

The present invention is directed to a new and improved method and apparatus in controlling calibration gas flow from a cylinder containing calibration gas to a gas or an air monitor. In particular, the present invention comprises a flow matching valve and regulator valve combination and methods for use thereof in various applications. For example, in calibrating a gas monitor, as the calibration gas flows into the gas monitor, any fluctuation in the quality and quantity of gas is matched by the flow regulator valve such that a constant flow is fed into the gas monitor and, in particular, to the sensor located in it.

In the preferred embodiment, the flow matching regulator valve efficiently delivers calibration gas to the sampling port of a pump driven gas monitor (and sensor) in constant flow, i.e., constant quantity and quality. A feature of the flow matching valve comprises a "T" junction added to a preset constant flow regulator valve along the tubing leading to the gas monitor. The T-junction serves as a pressure and flow compensator. In the preferred embodiment, the compensation is permitted by having a flexible cover at the bottom of the T leg so as to compensate for excess flow conditions as well poor flow conditions.

In an alternative embodiment, the T-junction permits venting-off excess flow conditions while sealing the T-junction when flow conditions are poor so as to permit a maximum flow of the calibration gas to the gas monitor. One feature of this alternate embodiment comprises a flow control relief ball which is located in the T-junction and floats according to pressure conditions in the T-junction. The float ball compensates for pressure and flow characteristics or conditions to obtain the required gas quality and quantity flowing into the gas monitor. A ball seat, on the other hand, forms a gas-tight seal during poor flow conditions.

A substantial advantage of the present invention includes the elimination of a sampling bag between the gas container and the gas monitor. The elimination of the sampling bag removes the possibility of gas waste and exposure to the user since "left-over" quantities of gas in the bag, under conventional technology, are simply exposed to the surrounding environment upon completion of calibration of the gas detector. Thus, waste gas is virtually eliminated under the present invention and loss of, sometimes expensive, calibration gas is kept at a minimum.

Another advantage of the present invention becomes apparent in the application of the present invention. It is apparent to one skilled in the industry that when calibrating a gas monitor, it is very important that the calibration have repeatable results, i.e., sampling gas must be available in quantities and quality such that each calibration attempt provide gas to the monitor that is consistent according standards required to obtain accurate readings for a particular sensor. The present invention thus offers and simulates field sampling conditions precisely to provide consistent repeatable samples of calibration gas to the monitor.

Additional objects, features and advantages will become apparent in the detailed description which follows.

DETAILED DESCRIPTION OF THE INVENTION

The present invention relates to methods and apparatus for regulating flow of calibration gas from its container to a gas monitor so that the monitor may be calibrated to obtain accurate readings of the environment. More particularly, but not by way of limitation, this invention relates to a method and apparatus for regulating the quantity and quality of gas flow from a portable gas container to a device that monitors environmental conditions that uses a flow regulator. The method concerns use of the flow regulator in calibrating environmental monitors.

1. Use of the Gas Monitor

Figure 1:
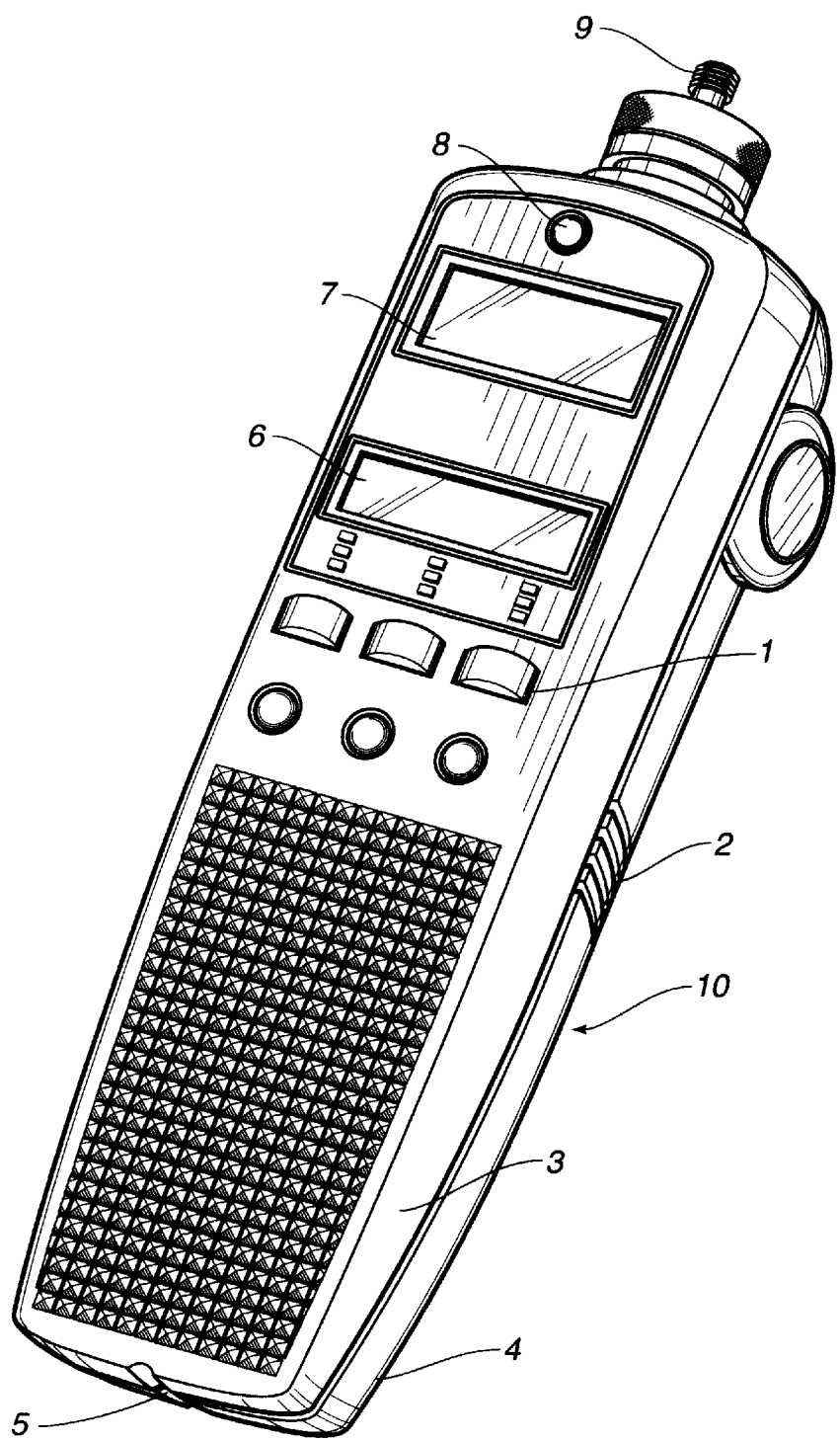
FIG. 1 is an illustration of a typical gas monitor.

Referring now to FIG. 1, a typical environmental monitor 10 is shown. Most monitors made today comprise a monitor 10 with data storage capabilities in conjunction with a basic microprocessor (not shown). As such information may be downloaded through a download port 5 and accurate records kept for repeated exposure environments. A typical monitor 10 has an audio alarm 2 as well as a visual alarm 8. In addition, a display 8 (either LCD or LED) provides a sensor reading, typically in parts per million (PPM). Typically, each reading is for a particular sensor. A monitor 10 usually has several sensors for each type of air component being tested. Most sensors (not shown) in gas monitors 10 are very "flow sensitive" and therefore for proper calibration to take place, it is critical and imperative that adequate and required gas flow be provide to the sensor during reading and calibration. Unless this constant flow and constant pressure is available, it is likely that a gas monitor 10 will be improperly calibrated. This point cannot be under-emphasized.

A gas monitor 10 also typically has a display 6 for calibration purposes. With aid of the calibration display 6, the monitor 10 is calibrated as sample calibration gas is fed to the monitor 10 through a sample inlet port 9. Calibration is completed by manipulating the calibration keys 1 provided on the face of most monitors 10. In some monitors, a filter is attached to the inlet port 9 so that any dust, particulate matter or moisture is removed for accurate reading. The monitor 10 is usually in a plastic case 3 that is rugged for field use. Power is usually provided through batteries 4 that may be rechargeable. The monitor 10 when exposed to the environment takes in samples of potentially hazardous air with the help of an aspirator pump (not shown). The sensor senses the composition of the air and readings are registered on the display 7. If the readings are made for repeated exposure purposes, a download port 5 transfers the stored data to a computer for record keeping purposes.

As the monitor 10, is used repeatedly and in different applications, the accuracy of the monitor 10 is lost. Typically, this loss in accuracy is compensated with calibration of the monitor 10. When readings appear to be faulty despite calibration, sensors usually have to be replaced.

2. Calibration of the Monitor

Figure 2:
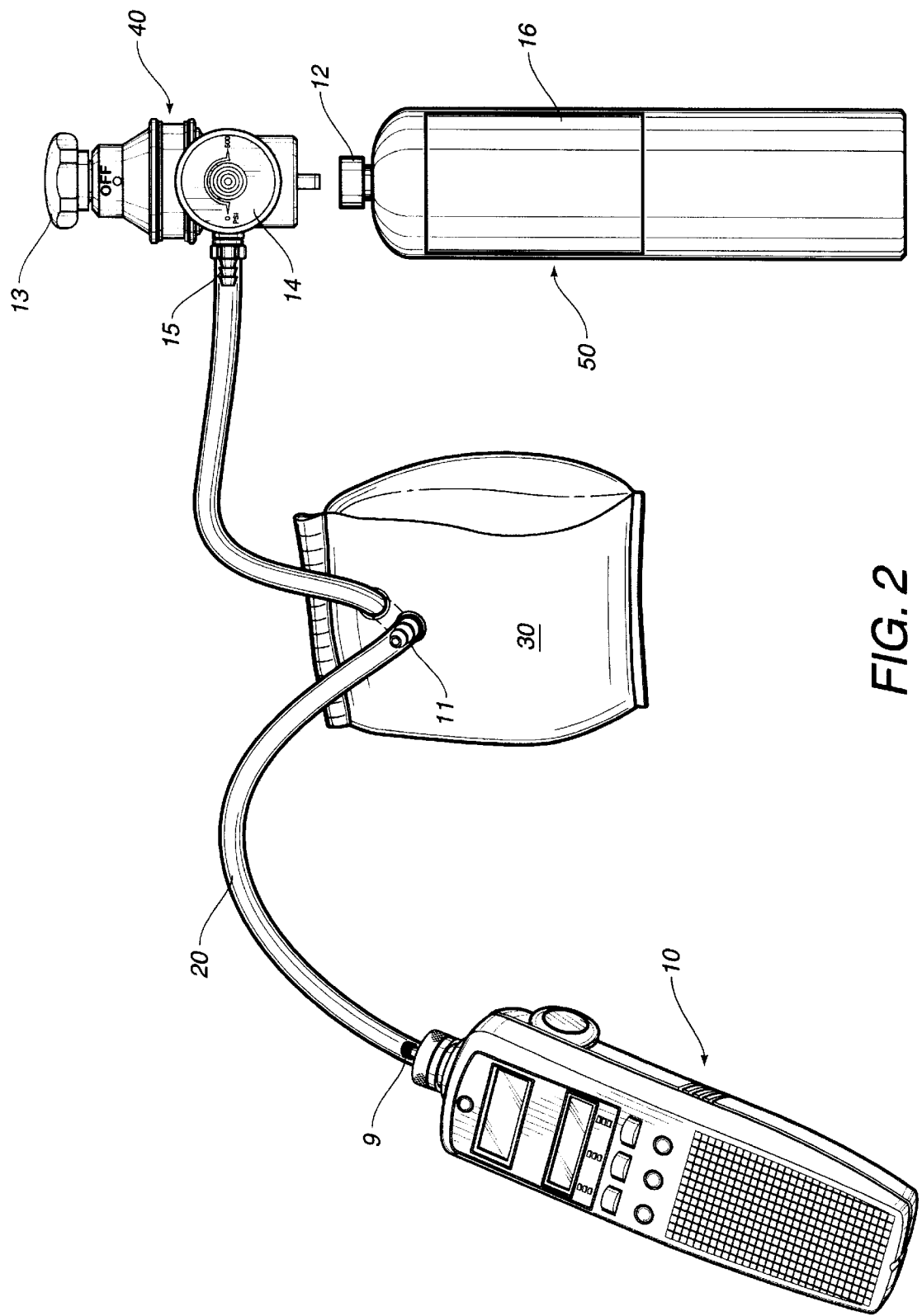
FIG. 2 is an illustration of the prior art conventional technology using a sampling bag.

FIG. 2 illustrates a typical calibration assembly as is conventionally (currently) available in the prior art. Referring now to FIG. 2, a monitor 10 is attached to tubing 20 which leads to a sampling bag 30. From the sampling bag 30, the (plastic) tubing 20 is connected to a regulator valve 40. The regulator valve 40, is then attached to a calibration gas cylinder 50 which contains single or multiple gases 16.

The sampling bag 30 acts like a balloon or a reservoir of sampling or calibration gas which can be manually manipulated. In other words, as the high pressured calibration gas 16 comes through the tubing 20 to the sampling bag (balloon) 30, the bag 30 acts to buffer the monitor 10 from the flow condition comprising a high pressure (and high velocity) calibration gas 16. It should be noted that pressure in the gas cylinder 50 varies drastically from one container to the next. For example, pressure in the cylinder ranges from 200 pounds per square inch (psi) to 4000 psi depending on the quantity and the type of gas that is to be stored. Thus, the buffering action occurs as a result of the expansive capacity of the bag 30 which inflates until the gas cylinder valve 40 is turned off. It is necessary to buffer the monitor 10 from such gas flow conditions having a relatively high pressure and velocity to avoid damage to an air monitor 10 and to obtain accurate readings.

It must be understood that to obtain the most accurate calibration of the air monitor, it is very important that the flow of the sampling gas must be smooth, consistent and most nearly simulate environmental or other required conditions while exposing the sensor to the correct quality and quantity of sampling or calibration gas. After the bag 30 has reached its maximum inflation capacity, the user under this system then turns off the regulator valve 40 and manually proceeds to squeeze the bag 40 to expose the inlet port 9 of the monitor 10 to the calibration gas 16. As previously stated, such calibration techniques have many disadvantages beside being cumbersome and unreliable.

Because of the very sensitive nature of various sensors located in an air monitor 10, the air monitors 10 are calibrated before every use to obtain accurate sensor readings. The checking for accuracy of sensors is accomplished by exposing the sensors to a known level of gas and taking readings for that sample; for example, a gas detector containing a combustible sensor, an oxygen sensor and a carbon monoxide sensor is exposed to a premixed gas of a known combustible, oxygen and carbon monoxide. If after exposure, the readings obtained from the gas detector agree with the predetermined and known levels of the premixed gas, the detector is in calibrated and may be safely used. However, if one or more of the readings varies from the known levels in the premixed gas, the detector must be calibrated according to the calibration instructions before the detector may be safely used. If after repeated calibration attempts, accurate sensor readings are not obtained, it is an indication that there is a fault in the unit or very possibly that the sensor itself has degraded to the point where It must be replaced. Thus, it is clear that by simply inflating a sampling bag 30 and then manually squeezing the bag 30 does not necessarily expose the monitor 10 to a reliable smooth and consistent flow condition, one that is under a relative constant pressure and velocity; and not only during a single calibration event but also from one calibration event to another. In other words, such calibration does not best simulate required conditions.

As one skilled in the industry may understand, the process of calibrating a gas detector is simply exposing a detector to a known clean air atmosphere as a zero reference, and additionally exposing the detector with a known gas concentration. Thus, by exposing the detector with clean air, the sensor will recognize or sense what an uncontaminated zero level is, and at the same time, by exposing the detector to a known concentration of gas, the sensor will recognize or sense what a given concentration above zero is. Adjusting the detector's displayed readings to a known concentration is called spanning the sensor. Thus, in summary, calibration is zeroing a sensor to a known air atmosphere and spanning it to a known concentration of gas.

Checking or viewing the calibration of a detector is different than the actual process of calibrating or recalibrating. For example, checking a sensor's reading against a known source, i.e., 35 parts per million (PPM) of carbon monoxide, is verifying what the detector displays when exposed to a concentration of 35 PPM. If the detector does display 35 PPM, it is in calibration. In the same circumstances, if the detector displays a reading other than 35 PPM, it is out of calibration and needs recalibration. The calibration, checking, and recalibration process is performed as a function of use and application. Most detector manufacturers recommend checking and verifying calibration before every use. The accuracy of the detector is affected by age, use, environmental conditions, saturation exposure, and many other such factors.

In summary, the calibration process generally involves: (1) selecting the sensor to be calibrated; (2) zeroing the sensor to clean air; (3) spanning the sensor to a known concentration of gas; and (4) saving the recalibrated adjustments for the sensor. The apparatus used to calibrate gas detectors include a calibration kit. The calibration kit comprises a gas bottle or container, a regulator valve, approximately 3 feet or tubing and tubing connectors for attachment to the sampling port in the gas monitor. The process of calibration is performed in a well ventilated location by slowly proceeding to open the gas container or cylinder by adjusting the regulator valve and allowing flow of the required gas to the detector. After about three or so minutes of gas flow, taking gas readings and verifying that the respective sensor's reading matches the known gas concentration parameter.

Problems, most often, encountered in this type of calibration process were previously discussed. In summary, one of the most significant problem is that the flow of gas to the detector is unregulated and therefore the readings are unreliable. For example, if the gas flow varies in flow quantity, the sensor reading will accordingly vary simply because the exposure is different at every moment in time as the reading is observed. Another significant problem encountered by the conventional method of calibration is that the draw rate of the pump in the gas monitor varies from pump to pump. This variance in pump draw rate cannot be compensated by the current monitor and calibration technology since the flow regulator valves operate at preset values. Another related problem is that the calibration gas cylinder pressure varies as the quantity of gas decreases. Similarly, as the battery power supply wears down, pump draw rates also begin to vary and again resulting in unreliable readings.

In the preferred and alternative embodiments, the present invention overcomes all of these problems by providing a gas flow condition that matches relative fluctuation and changes in flow pressures and/or velocities.

3. Construction of Flow Matching Regulator Valve

Figure 3:
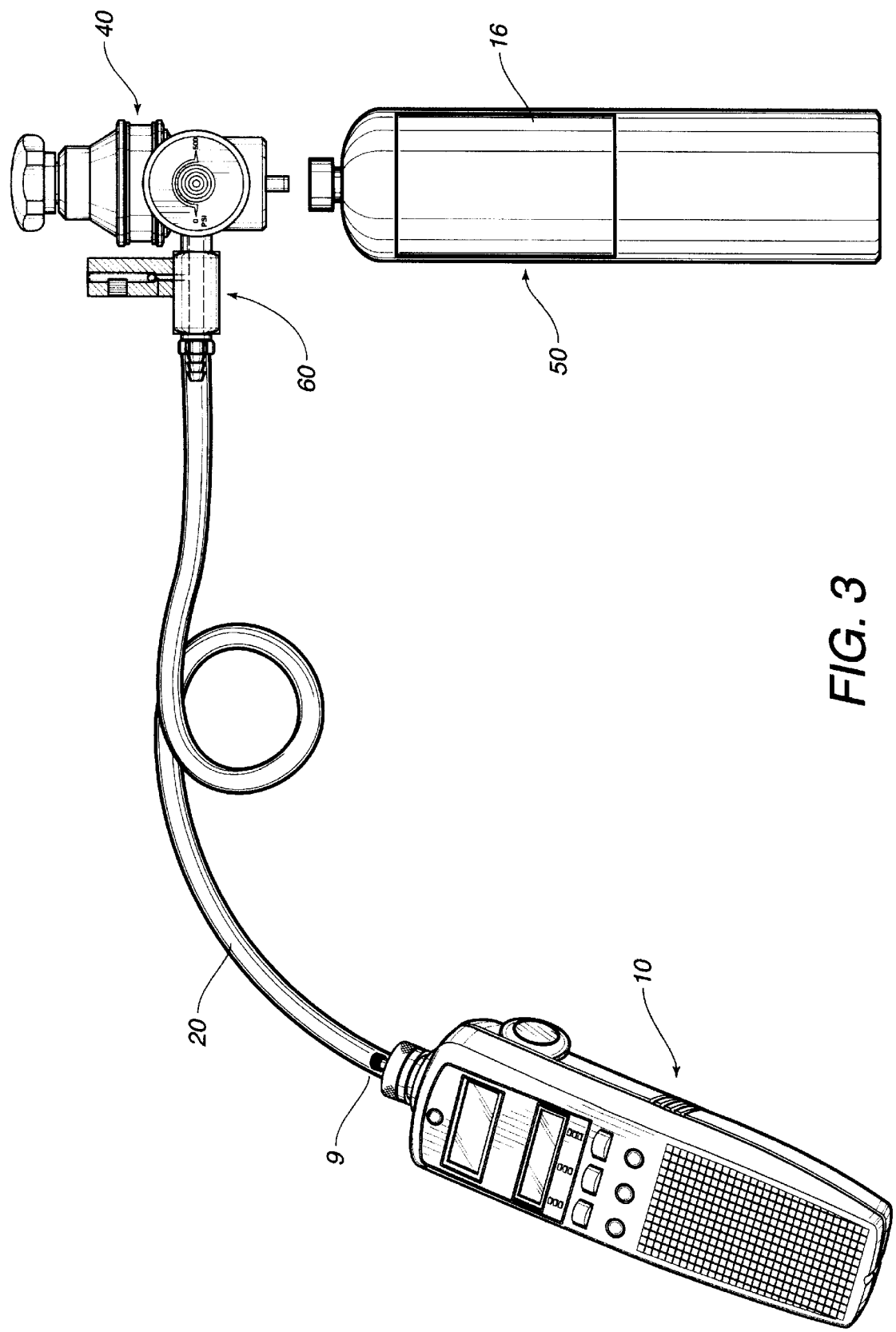
FIG. 3 is an illustration of the present invention using a T-junction flow regulator valve.

The present invention comprises a calibration kit (as shown in FIG. 3) that eliminates the cumbersome sampling bag 30 and connects the tubing 20 directly from the monitor 10 to the flow regulating valve 40 and attached gas cylinder 50. The flow regulator valve 40 has been modified with the addition of matching flow valve 60. The matching flow valve 60 best simulates the required calibration gas flow conditions to obtain the correct and accurate sensor readings. It eliminates the unreliable manual agitation of the sampling bag 30. Thus it eliminates any chances of improper gas exposure to the sensor. Accurate calibration is therefore the only outcome.

As shown in FIG. 3, a sampling gas cylinder 50 containing the appropriate known concentrations of gas 16 is released when the regulator valve 40 is opened. It should be noted that pressures in the gas cylinder 50 varies drastically from one container to the next. For example, pressure in the cylinder ranges from 200 pounds per square inch (psi) to 4000 psi depending on the quantity and the type of gas that is to be stored. The calibration gas 16 begins to flow through the regulator valve at certain flow quantities and pressure (flow conditions). This movement or flow condition is begun by the aspirator pumping action from the gas monitor 10. The calibration gas flows from the regulator valve 40 to a flow matching valve 60 which essentially compensates for any change in the flow conditions. The calibration gas 16 flow continues into the sampling port 9 and into the gas monitor 10 where calibration keys may be manipulated after readings are obtained.

Through the configuration of the present invention, unknown previously, calibration mat be repeated with reliability while eliminating any error due to human factors. This is so because one user may over inflate the sampling bag 30 while another may not refill the bag in time so that flow is interrupted thus producing a poor reading. In other words, it is impossible to obtain the required constant and consistent flow of calibration gas 16.

Figure 4:
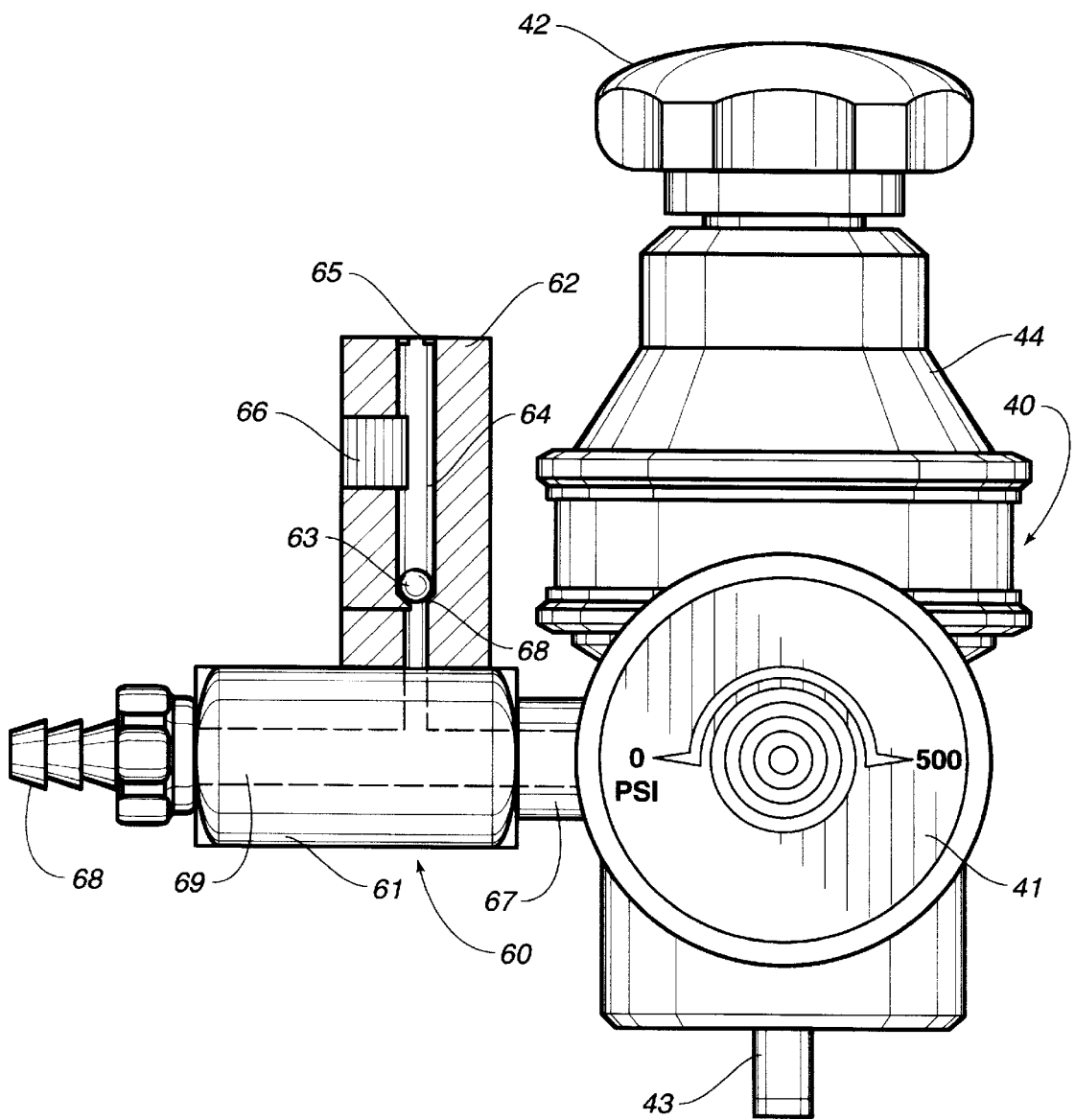
FIG. 4 is a cross-sectional view of the of the alternate embodiment.

One embodiment of the matching flow valve is shown in detail in FIG. 4 which simply eliminates any errors due to operation of the calibration process by different users. Another and the preferred embodiment is disclosed in FIG. 5. The matching flow valve of either embodiments establish a laminar gas flow condition over the sensor and any and all relatively lagged or inconsistent gas flow condition is eliminated. In other words, the calibration gas flow condition is maintained within a relative minor range of deviation while removing large fluctuations in the gas flow condition. As a result accurate readings may be taken and the monitor calibrated accordingly. Such accurate calibration is critical to proper functioning of the air monitor 10 and resulting safety in operation of the monitor in hazardous environments.

The details of the matching flow valves 60 will now be discussed. As shown in FIG. 2, a preset regulator valve 40 (prior art) is normally attached to the cylinder containing calibration gas. Gas flow from inside the cylinder 50 under great pressure begins to flow as the cylinder valve (not shown) is displaced or opened. The high pressure gas flow enters the preset regulator valve 40 and builds a certain amount of pressure against the surface of a diaphragm inside the preset regulator valve 40. As the diaphragm is displaced by the contents of the cylinder (calibration gas which may, for example, be at 1000 pounds per square inch or psi to 2000 psi), a stem in the preset regulator valve 40 is displaced from its seat (not shown) and the calibration gas escapes to an outlet 68. As a result, a high pressure jet shoots out of the outlet 68.

When attached to a gas monitor 10, this shooting jet is further affected by the aspirator pump in the monitor 10. This pump actually sucks the gas into the monitor 10 and attempts to establish laminar flow across the sensors. However, the aspirator pumps do not function at a constant rate for a variety of reasons already discussed herein. Because of this fluctuating "draw rate", there is either too much flow and pressure in the tubing and over the sensors or not enough flow creating a vacuum or non-flow over the sensors resulting in erroneous readings.

Figure 5:
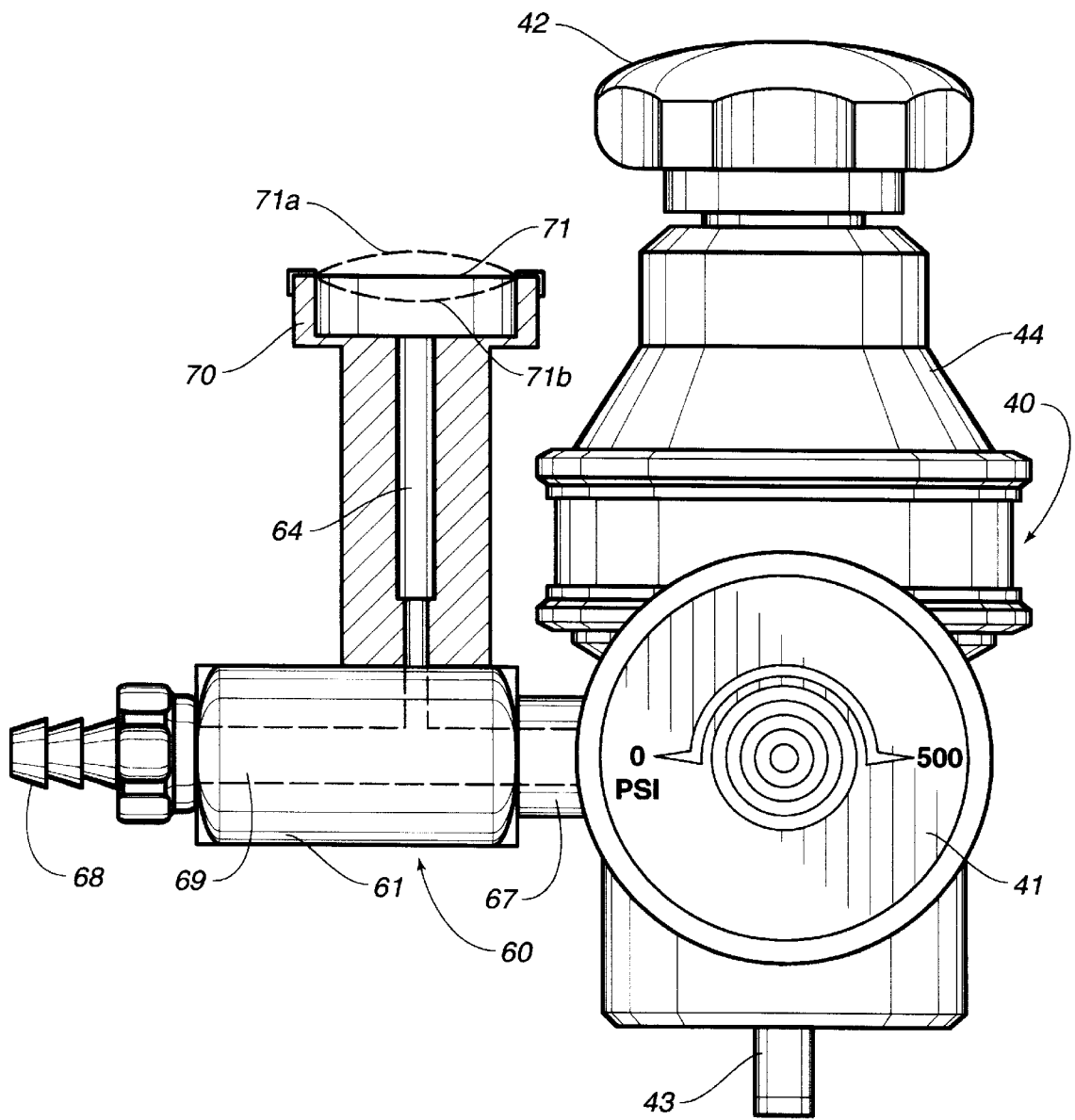
FIG. 5 is a cross-sectional view of the of the preferred embodiment.

The matching flow valve of either embodiment of the present invention is thus attached to the preset regulator valve 40 to avoid a jagged flow condition as shown in FIGS. 4 and 5. A relatively smooth flow condition is established by the matching flow valve 60 since it acts as a "vent-off" as in the case where too much flow is occurring while it shuts off the vent when not enough gas flow is present. In the latter case, the matching flow valve establishes a calibration gas flow condition where all of gas flow coming from the cylinder is directed straight into the monitor with the help of the aspirator pump. The simplicity of the flow matching valve 60 design creates an enormous efficiency in gas flow and establishes the required laminar flow condition over the sensors. In other words, the calibration gas flow condition is kept within a relatively range of deviation that permits the most efficient delivery of calibration gas to a sensor located within the air monitor.

In the alternate embodiment, as shown in FIG. 4, the matching flow valve 60 comprises a housing 61 having an axial passageway 69 through which flow occurs from one end (the inlet 67) to the other end (the outlet 68). A "vent-off" housing 62 is perpendicularly adjoined to the middle of the passageway 69 of housing 61. The vent-off housing comprises, in one embodiment, a cylindrical body 62 with an axial passageway 64. Thus the two passageways are connected perpendicularly and gas flow may also proceed perpendicularly in order to vent-off excess gas flow. The perpendicular axial passageway 64 has a ball 63 and seat 68 configuration so as establish flow in only one direction, i.e., away from the perpendicular junction in passageway 64 (vent-off only). In other words, air from outside the matching flow valve 60 may not enter inside the passageway 64 so as to contaminate the gas sample 16. On the other hand, gas flow from inside the matching flow valve 60 may escape to the outside should pressure exceed a certain given point. This point obviously depends upon the weight of the ball in the passageway 64. When vent-off occurs, the ball 63 is prevented from escaping the passageway 64 with the addition of a cover 65 which allows gas flow but prevents the ball 63 from leaving.

As flow is established, the preset regulator valve may be adjusted so as to maintain adequate flow. During this condition, the ball in the perpendicular passageway floats and the user may be assured that a proper amount of sample calibration gas is flow into the monitor. The vent-off housing 62 may preferably be made of polyurethane material so that the ball may be viewed. Markings 66 along the vent-off housing 62 may be made so that the user can maintain the ball 63 in a certain range of flow condition by adjusting the present regulator valve handle 42, along with monitoring the pressure gauge 41 attached to the preset valve regulator 40.

In another and the preferred embodiment, as disclosed in FIG. 5, the matching flow valve 60 is similar in most respects to alternate embodiment except one. The vent-off cover 71 is made of a flexible, rubber-like material. In the preferred embodiment, an actual vent-off does not occur, i.e., the calibration gas does not escape the flow matching valve assembly 60. Instead, the cover 71 is flexed outwardly 71a as gas flow pressure and volume increases beyond the capacity of the monitor 10 to take in the flowing gas and vice versa, i.e., the flexible material or cover 71 is sucked 71b in the housing 70 should the flow condition diminish to the point where a certain amount of vacuum is created in the tubing 20. In the preferred embodiment, the vent-off or perpendicular housing is enlarged where the cover is attached. This modification in configuration allows a greater volume of flowing gas to be agitated, i.e., a greater volume of lagged flow is permitted. The principle of operation is identical to that discussed previously herein in the alternate embodiment. As the flow volume and pressure in the tubing increases, the flexible cover compensates for this increase in flow condition. On the other hand, when flow conditions decrease and the aspirator pump is seeking a great flow capacity than is available, the flexible cover, again, compensates.

One chief advantage the preferred embodiment provides over the alternate embodiment is that the position of the flow matching valve may in any direction irrespective of the gravity. The alternate embodiment, on the other hand, may be limited in certain circumstances to conditions of gravity since the ball in the vent-off housing may get stuck in the direction of the gravity.

It is apparent from the design characteristics the advantages the present invention provides over the prior art Principal among these advantages includes providing adequate and consistent flow conditions to the sensor so that a gas monitor may be accurately calibrated for safe use. The present invention provide a simple design yet overcomes many of the disadvantages that existed in the prior art.

Changes and modifications in the specifically described embodiments may be carried out without departing from the scope of the invention which is intended to be limited only by the scope of the appended claims. For example, a change in the location of the flow matching valve would not substantial deviate from the present invention. Thus, attaching a flow matching valve to the monitor make good sense but does not depart from the invention presented herein. Placing the flow matching valve with monitor gives many additional advantages and makes the monitor much more flexible. All such changes are intended to be incorporated in the present invention.

We claim:

1. An apparatus for monitoring environmental air quality comprising:

a) an air monitor for detecting components of air in an environment; and b) a calibration kit for calibrating the air monitor comprising:

i) a gas cylinder containing a calibration gas for use in calibrating the air monitor by flowing the calibration gas over a sensor located within the air monitor;

ii) a preset regulator valve connected to the gas cylinder for permitting a predetermined calibration gas flow condition out of the gas cylinder;

iii) a flow matching valve connected to the preset regulator valve for permitting the calibration gas flow condition to be maintained within a relative range of flow condition deviation; and wherein the flow matching valve comprises: a first housing with an axial passageway for permitting gas flow therein; a second housing connected perpendicularly to the first housing and having an axial passageway for permitting gas flow therethrough; a ball located within the second housing for preventing environmental air from entering the second housing while permitting gas flow to the environment; the second housing having a ball seat for providing an air-tight seal when the ball is nudged against the ball seat; and a cover attached to the second housing for preventing the ball from escaping the second housing while allowing gas flow therethrough; and iv) a tube connecting the flow matching valve to the air monitor for transporting the calibration gas to the air monitor.

2. The apparatus of claim 1, wherein the air monitor further comprises:

a) a microprocessor for processing sensed data from the sensor located within the air monitor;

b) an information storage medium for storing data sensed by the sensor located within the air monitor;

c) a download port for downloading stored data in the information storage medium.

3. A method for monitoring environmental air quality comprising:

a) calibrating an air monitor using a calibration kit comprising:

i) a gas cylinder containing a calibration gas for use in calibrating the air monitor by flowing the calibration gas over a sensor located within the air monitor;

ii) a preset regulator valve connected to the gas cylinder for permitting a predetermined calibration gas flow out of the gas cylinder;

iii) a flow matching valve connected to the preset regulator valve for permitting the calibration gas flow condition to be maintained within a relative range of flow condition deviation; and wherein the flow matching valve comprises: a first housing with an axial passageway for permitting gas flow therethrough; a second housing connected perpendicularly to the first housing and having an axial passageway for permitting gas flow therein; a ball located within the second housing for preventing environmental air from entering the second housing while permitting gas flow to the environment; the second housing having a ball seat for providing an air-tight seal when the ball is nudged against ball seat; and a cover attached to the second housing for preventing the ball from escaping the second housing while allowing gas flow therethrough; and iv) a tube connecting the flow matching valve to the air monitor for transporting the calibration gas to the air monitor; and b) testing the environmental air quality using the air monitor.

4. The method according to claim 3, further comprising:

maintaining the calibration of the air monitor within a tolerance limit specified for the sensor located within the air monitor by calibrating the air monitor prior to each use.

5. A method for calibrating an air monitor prior to each use comprising:

a) using a calibration kit comprising:
  i) a gas cylinder containing a calibration gas for use in calibrating the air monitor by flowing the calibration gas over a sensor located within the air monitor;
  ii) a preset regulator valve connected to the gas cylinder for permitting a predetermined calibration gas flow out of the gas cylinder;
  iii) a flow matching valve connected to the preset regulator valve for permitting the calibration gas flow condition to be maintained within a relative range of flow condition deviation; and wherein the flow matching valve comprises: a first housing with an axial passageway for permitting gas flow therethrough; a second housing connected perpendicularly to the first housing and having an axial passageway for permitting gas flow therein; a ball located within the second housing for preventing environmental air from entering the second housing while permitting gas flow to the environment; the second housing having a ball seat for providing an air-tight seal when the ball is nudged against the ball seat; and a cover attached to the second housing for preventing the ball from escaping the second housing while allowing gas flow therethrough; and
  iv) a tube connecting the flow matching valve to the air monitor for transporting the calibration gas to the air monitor;

b) selecting at least one sensor located within the air monitor to be calibrated;

c) zeroing the selected sensor to clean air;

d) spanning the selected sensor to a known concentration of calibration gas; and e) saving a recalibrated adjustment value for the selected sensor in the air monitor.

* * * * *